United States Patent [19]

Jolly et al.

[11] Patent Number: Plant 5,579

[45] Date of Patent: Nov. 5, 1985

[54] ROSE PLANT 'SNOW BRIDE'

[75] Inventors: Betty J. Jolly, Sea Girt, N.J.; Nelson F. Jolly, Galena, Md.

[73] Assignee: Jolly's Rosehill Farm of Kent, Inc., Galena, Md.

[21] Appl. No.: 497,180

[22] Filed: May 23, 1983

[51] Int. Cl.[4] ..... A01H 5/00

[52] U.S. Cl. ..... Plt./8

[58] Field of Search ..... Plt./7-10

*Primary Examiner*—James R. Feyrer

*Attorney, Agent, or Firm*—Vincent G. Gioia

[57] ABSTRACT

A new miniature rose variety of near white coloring having white outer petals and near chrome-yellow flower centers.

1 Drawing Figure

The present invention relates to a new and distinct variety of rose plant of the miniature rose class, which was originated by my crossing as seen parent the rose known as "Avandel" (U.S. Plant Pat. No. 4,366) and the rose known as "Zinger" (U.S. Plant Pat. No. 4,293) as pollen parent. The denomination of the new rose is "Snow Bride".

Among the novel characteristics possessed by this new variety which distinguish it from its parent and all other varieties of which I am aware are its relatively large (for a miniature) flowers of unusual near white coloring having near chrome-yellow flower centers and high centered, exhibition form. The petals have a deeper chrome-yellow hue at their lower segment toward the point of petal attachment and shade to white at the outer edge of the petals. Asexual reproduction by budding of the new variety as performed in Kent County, Md., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "158B" is plate 158B of The Royal Horticultural Society Colour Chart.

Parentage: Seedling.
*Seed parent.*—"Avandel".
*Pollen parent.*—"Zinger".
Class: Miniature.

The following observations are made of specimens grown in Kent County, Md. during the month of August.

1. FLOWER

Blooming habit: Continuous.

A. Bud:
(1) *Size.*—Medium.
(2) *Form.*—Ovoid, pointed.
(3) *Color.*—After sepals fall, near chrome yellow petal undersurface (158B to 158A) of main portion of the petal is first visible, with the deeper hue, 158A, at the point of petal attachment shading into 158B and then still lighter becoming near white toward the outer petal edge.
(4) *Sepals.*—Slightly shorter than bud, light green, ordinary shape.
(5) *Peduncle.*—Length — About 2 cm. Strength — Medium. Color — Near 144A.

B. Bloom:
(1) *Size.*—Average size when fully expanded — about 5 cm.
(2) *Borne.*—Primarily one to a stem
(3) *Form.*—High centered, becoming flat upon opening.
(4) *Petalage.*—Number of petals under normal conditions — About 30 to 35.
(5) *Color.*—After sepals fall and buds unfurl, the pronounced near chrome-yellow coloring of the lower segments of the undersurface of the petals near the point of attachment becomes less visible and the near white flower coloring predominates. At the $\frac{1}{3}$ to $\frac{1}{2}$ open stage, the white (155A and 155C) color of the outer petals are most prominent. Nonetheless, the flower center continues to display the yellow-white coloring of the lower segments of the petals. The flower colorings lighten further upon aging. The general tonality from a distance is white.

C. Petals:
(1) *Texture.*—Medium.
(2) *Appearance.*—Inside satiny, outside satiny.
(3) *Form.*—Fan shaped but often pointed.
(4) *Arrangement.*—Regularly arranged, shingle-like.
(5) *Petaloids in center.*—Few.
(6) *Persistence.*—Drop off cleanly.
(7) *Fragrance.*—Slight.
(8) *Lasting quality.*—About one week on the plant or after cutting.

2. REPRODUCTIVE ORGANS

A. Stamens, filaments and anthers:
(1) *Arrangement.*—Stamens regularly arranged around styles.
(2) *Color.*—Near 17B.

B. Pollen:
*Color.*—Near 17B.

C. Styles: Even, short.

D. Stigmas:

*Color.*—Near 47B.

E. Hips: Globular, about 1 cm., reddish coloring, seeds do not protrude.

3. PLANT

A. Form: Compact.

B. Growth: Vigorous, uniform branching.

*Height attained.*—About 45 cm.

C. Foliage: Usually compound 5 leaflets.

(1) *Size.*—Medium.

(2) *Quantity.*—Abundant.

(3) *Color.*—New foliage: Upper side — Near to 178A. Under side — Near to 165A. Old foliage: Upper side — Near 137A. Under side — Near 147B.

(4) *Shape.*—Oval, pointed.

(5) *Texture.*—Upper side is semi-glossy and under side is matte.

(6) *Edge.*—Serrated.

(7) *Serration.*—Serrate.

(8) *Leaf stem.*—Color — Near to 146A. Under side — Near 147B.

(9) *Stipules.*—Medium, slightly bearded.

(10) *Resistance to disease.*—Blackspot — Average. Mildew — Average.

D. Wood:

(1) New wood.—Color — Near 144A. Bark — Smooth.

(2) *Old wood.*—Color — Near 144A. Bark — Smooth.

E. Thorns:

(1) *Thorns.*—Quantity (main stalk) — Ordinary. On laterals from stalk — Ordinary. Form — Flat base. Length — Small. Color — Orange red. Position — Irregular.

(2) *Prickles.*—Medium.

F. Winter hardiness: Winter hardy.

I claim:

1. A new and distinct variety of rose plant of the miniature rose class, substantially as shown and described, characterized particularly by heavily petaled, relatively large, high centered, near white flowers with yellow-white toned centers borne primarily one to a stem.

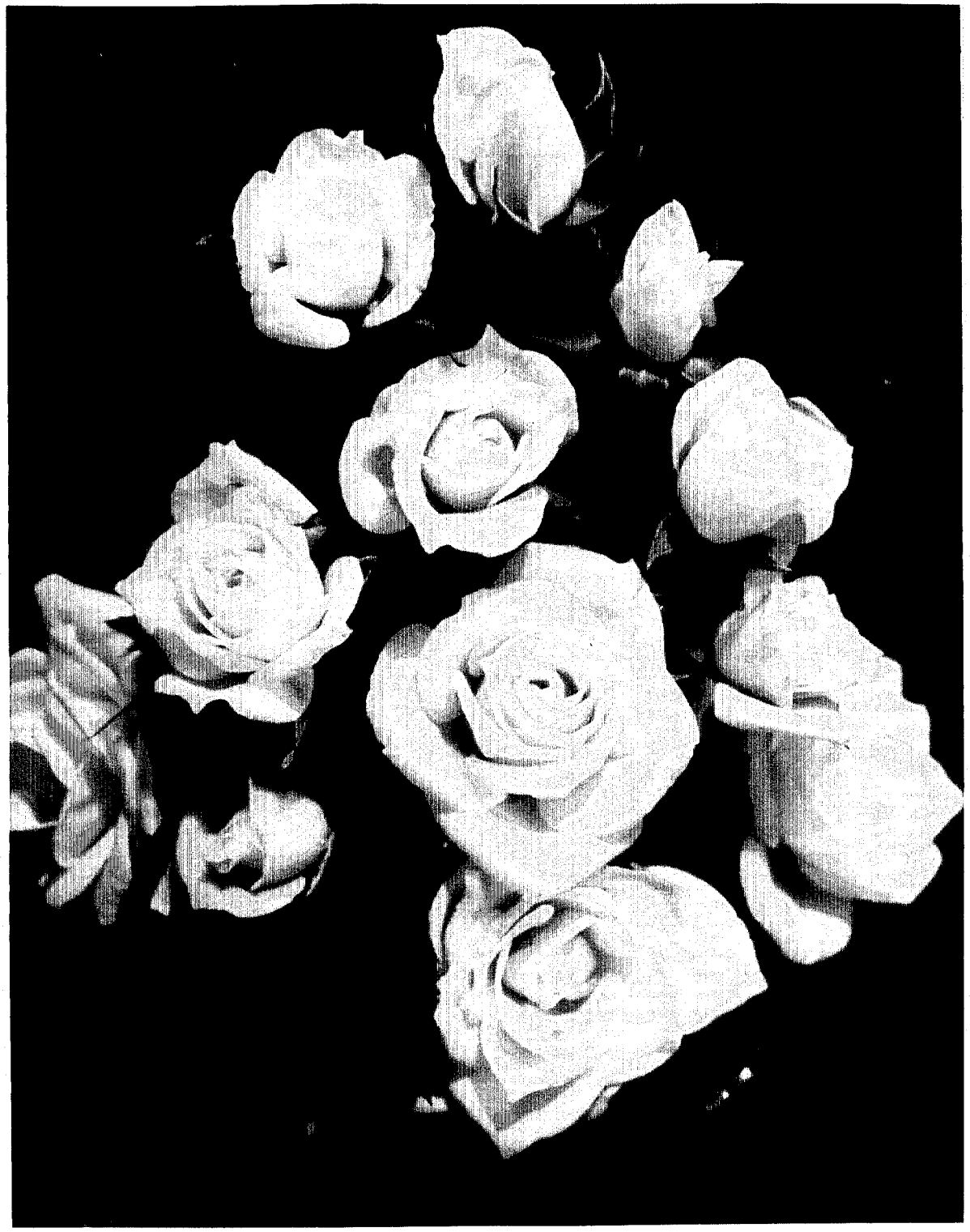

* * * * *